US005478338A

United States Patent [19]
Reynard

[11] Patent Number: 5,478,338
[45] Date of Patent: Dec. 26, 1995

[54] FIBER OPTIC SLEEVE FOR SURGICAL INSTRUMENTS

[76] Inventor: Michael Reynard, 846 Bronze La., Los Angeles, Calif. 90049

[21] Appl. No.: 125,774

[22] Filed: Sep. 24, 1993

[51] Int. Cl.⁶ .................................................. A61B 17/32
[52] U.S. Cl. ................... 606/15; 607/89; 606/17
[58] Field of Search ...................... 606/15, 16, 17, 606/10, 11, 12; 607/88, 89

[56] References Cited

U.S. PATENT DOCUMENTS

| | | |
|---|---|---|
| 3,357,423 | 12/1967 | Winchester et al. . |
| 3,699,950 | 10/1972 | Humphrey, Jr. et al. . |
| 3,809,072 | 5/1974 | Ersek et al. . |
| 3,888,004 | 6/1975 | Coleman . |
| 4,273,109 | 6/1981 | Enderby . |
| 4,398,790 | 8/1983 | Righini et al. . |
| 4,517,974 | 5/1985 | Tanner . |
| 4,526,170 | 7/1985 | Tanner . |
| 4,537,193 | 8/1985 | Tanner . |
| 4,538,608 | 9/1985 | L'Esperance, jr. . |
| 4,551,129 | 11/1985 | Coleman et al. . |
| 4,589,404 | 5/1986 | Barath et al. ................. 606/17 |
| 4,657,014 | 4/1987 | Edelman et al. . |
| 4,681,104 | 7/1987 | Edelman ..................... 606/17 |
| 4,744,360 | 5/1988 | Bath . |
| 4,772,093 | 9/1988 | Abele et al. . |
| 4,778,247 | 10/1988 | Carpenter . |
| 4,782,819 | 11/1988 | Adair ............................. 128/6 |
| 4,860,743 | 8/1989 | Abela ........................... 606/15 |
| 4,865,029 | 9/1989 | Pankratov et al. . |
| 4,870,952 | 10/1989 | Martinez . |
| 4,895,145 | 1/1990 | Joffe et al. .................... 606/15 |
| 5,041,108 | 8/1991 | Fox et al. ..................... 606/15 |
| 5,061,255 | 10/1991 | Greenfeld et al. ........... 606/266 |
| 5,074,861 | 12/1991 | Schneider et al. . |
| 5,121,740 | 6/1992 | Uram . |
| 5,122,328 | 5/1992 | Taboada et al. . |
| 5,151,098 | 9/1992 | Loertscher . |
| 5,213,092 | 5/1993 | Uram . |
| 5,257,988 | 11/1993 | L'Esperance, Jr. . |
| 5,263,950 | 11/1993 | L'Esperance, Jr. . |
| 5,275,593 | 1/1994 | Easley et al. . |
| 5,300,061 | 4/1994 | Easley et al. . |
| 5,318,560 | 6/1994 | Blount et al. . |
| 5,323,766 | 6/1994 | Uram . |
| 5,324,282 | 6/1994 | Dodick . |
| 5,351,168 | 9/1994 | Easley . |
| 5,356,407 | 10/1994 | Easley et al. . |
| 5,394,492 | 2/1995 | Hwang . |

FOREIGN PATENT DOCUMENTS

| | | |
|---|---|---|
| 1245726 | 11/1988 | Canada . |
| 2079429 | 4/1993 | Canada . |
| 0501034A1 | 2/1992 | European Pat. Off. . |
| 9101687 | 2/1991 | WIPO ..................... 606/12 |

OTHER PUBLICATIONS

Arch Ophthalmol, vol. 110, Dec., 1992, pp. 1748–1750: "Endoscopy of the Lacrimal Outflow System", Fein et al.
Arch Ophthalmol vol. 111, Jul., 1993, pp. 903–904: "Neodymium–YAG Laser Phacolysis of the Human Cataractous Lens".
Ophthalmology, vol. 99, Dec., 1992: "Ophthalmic Laser Microendoscope Ciliary Process Ablation in the Management of Neovascular Glaucoma" and Ophthalmic Laser Microendoscope Endophotocoagulation, Uram; pp. 1823 and 1829–1832, respectively.

(List continued on next page.)

Primary Examiner—Stephen C. Pellegrino
Assistant Examiner—Sonya C. Haris-Ogugua
Attorney, Agent, or Firm—Henry M. Bissell

[57] ABSTRACT

A disposable fiber optic sleeve for attachment at the forefront of a surgical instrument. The sleeve is an elongated tubular shape and incorporates multiple fiber optic bundles for transmission of visible light to enhance intraocular visualization. Additional bundles of optical fibers may provide for the application of laser beam and video transmission to intraocular tissue. The sleeve is constructed of inexpensive plastic materials and is designed to be disposable after a single or several uses.

17 Claims, 2 Drawing Sheets

OTHER PUBLICATIONS

*Ophthalmology*, vol. 100, No. 7, Jul., 1993, pp. 1066–1070: "Experimental Endoscopic Goniotomy", Joos et al.

Brochures under the title "The Grieshaber Light Source and Family of Accessories", Grieshaber & Co., Inc., 3000 Cabot Boulevard West, Langhorne, Pa. 19047.

Brochure: "Simultaneous Illumination, Viewing and Laser Delivery" (five pages), Endo Optiks, 39 Sycamore Avenue, Little Silver, N.J. 07739.

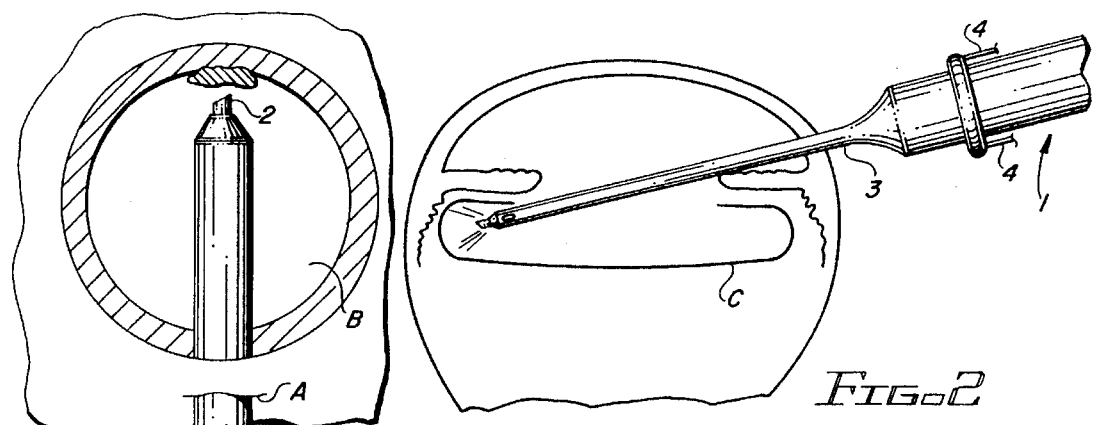
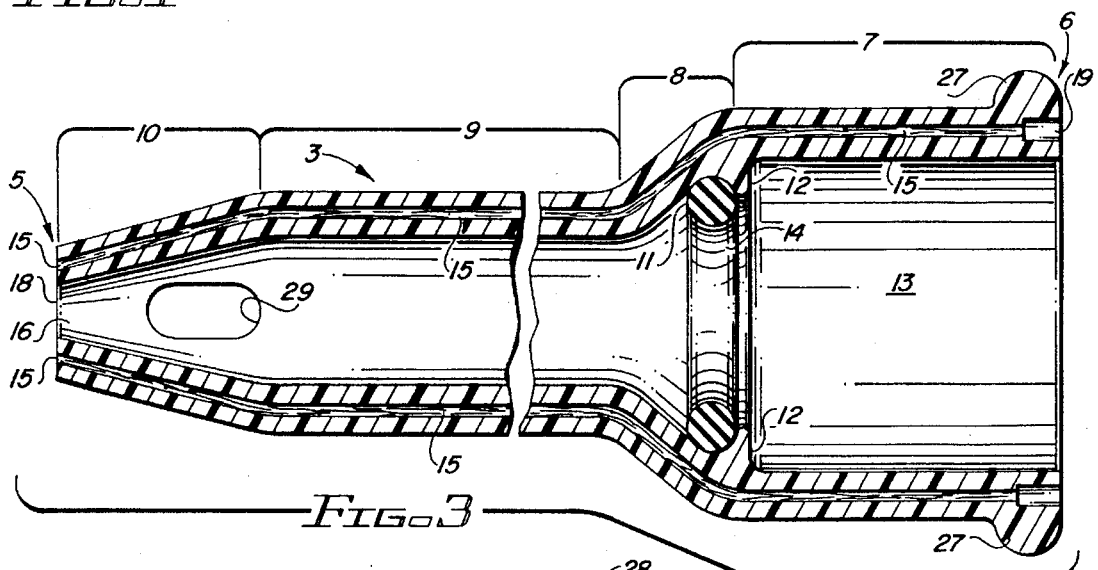
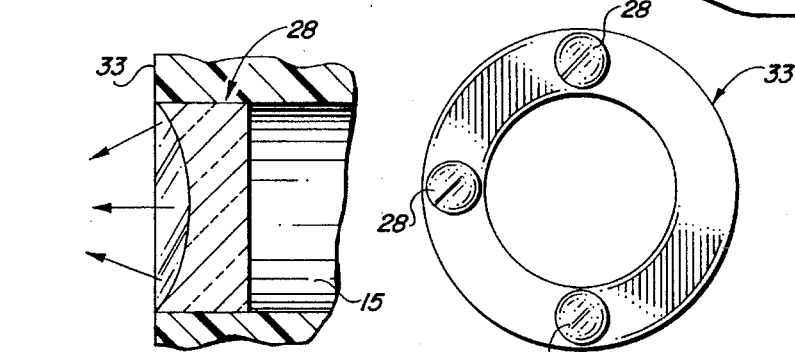

FIBER OPTIC SLEEVE FOR SURGICAL INSTRUMENTS

BACKGROUND OF THE INVENTION

1. Field of the Invention

This invention relates to surgical devices and, more particularly, to devices for effecting the transmission of light for endoillumination, intraocular endoscopy, or laser application to intraocular tissue.

2. Discussion of the Related Art

The most widely accepted prior art means for performing intraocular surgery in the anterior segment of the eye comprise a variety of instruments designed for irrigation, ablation, cutting and removal of tissue. Separate instruments for irrigation, illumination and laser application are known, but they have the disadvantage of requiring multiple surgical openings in the eye and may be cumbersome to operate for the surgeon. Multiple surgical openings in the eye and multiple surgical instruments add to the risk of complications and increase the difficulty of the surgical procedure. Surgical instruments that combine water infusion, suction and light conducting elements in a single probe have been described, but they have the inherent physical limitations imposed by side-by-side conducting channels. Another problem that arises in the use of complex multiple-element surgical instruments is the cost and labor of repeated sterilization.

Examples of ophthalmic instruments of the type described are commercially available from Grieshaber & Co., Inc., 3000 Cabot Boulevard West, Langhorne, Pa. 19047. These are shown in company brochures under the title "The Grieshaber Light Source and Family of Accessories".

Recent reports of specific cases in which prior art instruments of the type described are used may be found in *Arch Ophthalmol* Vol. 111, July 1993: "Neodymium-YAG Laser Phacolysis of the Human Cataractous Lens" and *Ophthalmology*, Vol. 100, Number 7, July 1993: "Experimental Endoscopic Goniotomy". The former describes a performance of Nd-YAG laser phacolysis on a particular patient for the removal of a nuclear sclerotic cataract. The latter report describes the use of an endoscope coupled to another surgical instrument in experimental surgery on porcine cadaver eyes designed to lead to the use of a tiny endoscope attached to a goniotomy needle for the treatment of primary infantile glaucoma. Both of these arrangements are subject to the deficiencies described hereinabove.

OBJECTS OF THE INVENTION

The primary object of the present invention is to provide an attachment for surgical devices, specifically adaptable for intraocular surgery, that provides illumination, endoendoscopy, and a means for laser beam delivery. The device is economical in its construction so as to be inexpensively re-sterilized and reused or simply discarded after each use because of its low cost. The device comprises a fiber optic sleeve which is easily and inexpensively fabricated and useful in conjunction with a variety of surgical procedures. For purposes of illustration, arrangements of the invention will be discussed in relation to a preferred embodiment for ophthalmic use and with respect to various considerations involved in the recommended utilization of the arrangements disclosed herein. The invention is not so limited, however, and it is entitled to the scope of protection afforded by the accompanying claims.

Illumination.

The vast majority of intraocular surgical procedures involve visualization by the surgeon through a high-powered microscope using intense coaxial illumination. It is well-documented that direct and intense microscope illumination may be damaging to the retina; macular edema with corresponding reduction of vision is the primary side effect. As an alternative, focal illumination directed at an oblique angle and in a direction away from the retina can enable the surgeon to reduce the amount of direct microscope light necessary to perform ocular surgery, thereby minimizing potential retinal light toxicity.

A common problem in the present state of the art is that visualization of the proximal tip of the surgical device is often impeded when blood, scar tissue, or inflammatory debris is present. During normal phacoemulsification of a cataract in the presence of a small pupil, the proximal tip of the surgical device is obscured behind the iris. Consequently, there is a higher risk of inadvertent rupture of the lens capsule, vitreous prolapse into the anterior chamber and retinal problems, all of which are associated with visual loss. Use of a fiber optic sleeve in accordance with the invention permits visualization of the anterior portion of the surgical instrument by virtue of transillumination through the iris leaf or opaque media. Moreover, it is often difficult for the operating surgeon to judge the depth of cataract or other intraocular structures. Surgical intervention to an excessive depth can lead to complications resulting in visual loss. Focal illumination at an oblique angle with a fiber optic sleeve of the invention can enhance the operating surgeon's ability to judge the depth of intraocular structures and thereby lessen the possibility of surgical mishap.

Endoscopy.

Direct visualization of vital intraocular structures during surgery can be realized with the image-carrying capacity of the fiber optic sleeve of the invention. Intraocular microendoscopy can be utilized to confirm positioning of haptics of a posterior chamber intraocular lens. At present, the surgeon is not able to visually inspect and confirm the location of posterior chamber intraocular lens haptics. Malpositioned haptics may result in lens decentration subsequent to surgery. Decentration of lens implants causing visual loss or distortion necessitates corrective surgical procedures. Visualization of intraocular lens haptics in combination with positioning adjustments at the time of surgery can prevent intraocular lens decentration.

Laser Application.

Finally, the fiber optic sleeve of my invention permits application of laser illumination for intraocular tissue coagulation and ablation. The present invention provides a means to couple laser energy delivery with simultaneous illumination and visualization. Lasers capable of transmission through the fiber optic sleeve include Holmium:YAG (2.1 um wavelength), Thulium:YAG (1.96 um wavelength), Erbium:YAG (2.94 um wavelength), Hydrogen Fluoride (2.7–3.0 um wavelength), Deuterium Fluoride (3.7–4.1 um wavelength), Carbon Monoxide (5.3–5.7 um wavelength), Carbon Dioxide (10.6 um wavelength), Argon Fluoride (193 nm wavelength), Krypton Fluoride (248 nm wavelength), Diode Red (670 nm wavelength), Xenon Chloride (308 nm wavelength), Argon Blue (488 nm wavelength), and Argon Green (514 nm wavelength).

Laser ablation of ciliary body processes responsible for producing excessive intraocular fluid, and for creation of a drainage fistula through the sclera, permits control of elevated intraocular pressure and glaucoma. Laser photocoagulation of ciliary body processes for treatment of glaucoma used in the present art involves external treatment through peripheral iridectomies. The effectiveness of this treatment is significantly limited because only a small number of ciliary processes can be treated. In the presently preferred embodiment, the endolaser and endoscopic capabilities permit treatment of the ciliary processes for at least 180 degrees, allowing for an enhanced laser therapeutic effect.

Manual methods used for anterior lens capsulotomy have inherent disadvantages that includes inadvertent radial capsule tears. Significant radial capsule tears are likely to result in complications such as vitreous prolapse or implant subluxation. Such disturbances can reduce or eliminate the visual benefit of an eye operation, or delay the healing process. Anterior capsulotomy with laser allows for controlled and precision capsulotomy edges unattainable by manual methods.

In addition, laser application through the fiber optic sleeve is useful as a substitute or adjunct for ultrasonic phacoemulsification in cataract surgery.

In summary, from the foregoing discussion it will be appreciated that the fiber optic sleeve of the present invention is particularly beneficial when used with implements for intraocular surgery. It is of simple and inexpensive construction so that it may be re-sterilized by gas or readily disposable after a single use. In addition, the fiber optic sleeve provides an advantage for the anterior segment surgeon because it provides focal illumination and capability for simultaneous laser application.

SUMMARY OF THE INVENTION

In brief, arrangements in accordance with the present invention comprise a fiber optic sleeve device particularly adapted to be installed on a phacoemulsification instrument so as to provide a focal light source at the point of surgery. The conventional phacoemulsification instrument for which the fiber optic sleeve of the present invention is adapted consists of a handpiece containing a magneto-strictive ultrasonic mechanism that activates a hollow, 1 mm titanium needle covered with a soft silicone sleeve. The needle is driven by the ultrasonic mechanism to vibrate forty thousand times per second longitudinally in the axis of the needle. The mechanical vibration transforms the patient's lens into an emulsion, hence the name "phacoemulsification". One such instrument is marketed by Mentor O&O, Inc., 3000 Longwater Drive, Norwell, Mass. 02061.

As the cataract is dissected by the high frequency phacoemulsification probe, it is sucked into the hollow titanium needle. Since removal of intraocular fluid must be balanced with the introduction into the eye with an equivalent amount of fluid, an irrigating solution is passed between the silicone sleeve and outer wall of the titanium needle. The silicone sleeve presently in use serves only as a conduit to direct flow of saline solution.

The present invention involves the incorporation of a specially designed fiber optic sleeve that substitutes for the presently used silicone sleeve. Thus, the fiber optic sleeve of the present invention provides for the transmission of the irrigating solution to the site of the cataract while also transmitting focal light to the point of surgery.

BRIEF DESCRIPTION OF THE DRAWINGS

A better understanding of the present invention may be realized from a consideration of the following detailed description, taken in conjunction with the accompanying drawing, in which:

FIG. 1 is a general schematic view showing a human eye in the process of undergoing a surgical procedure;

FIG. 2 is an enlarged schematic cross-sectional view showing a fiber optic sleeve and phacoemulsification instrument combination of the invention as used in the removal of a cataract from a human eye;

FIG. 3 is an enlarged schematic sectional view of the fiber optic sleeve of FIG. 2;

FIG. 3A is a schematic view, partially broken away, of a portion of the fiber optic sleeve of FIG. 3 showing one particular coupling arrangement;

FIG. 3B is a schematic view, partially broken away, of an alternative arrangement to that of FIG. 3A;

FIGS. 4A and 4B show alternative termination elements for use with the arrangement of FIG. 4;

DETAILED DESCRIPTION OF THE PREFERRED EMBODIMENTS

Figure 5A:
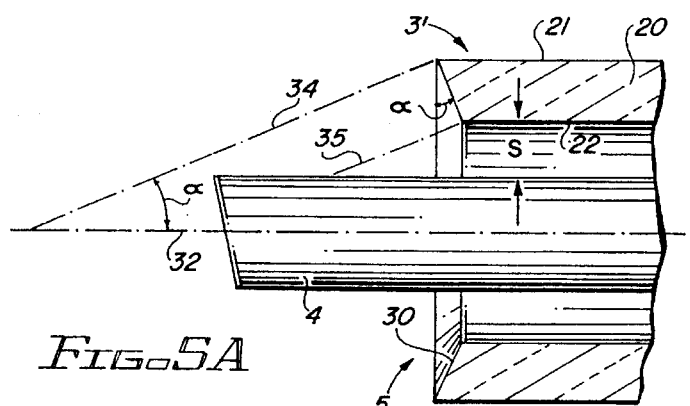
FIG. 5A is an enlarged schematic view of a portion of the embodiment of FIG. 5.

FIG. 1 shows a human eye in the process of undergoing a surgical procedure using a phacoemulsification instrument 1 of conventional type with a sleeve 1A and needle 2. The instrument 1 is inserted through a scleral flap eye incision A and into the anterior chamber B.

FIG. 2 schematically represents a similar procedure being performed with the substitution of a fiber optic sleeve in accordance with the present invention. FIG. 2 shows an enlarged cross-sectional view of the eye. The cataract has been removed by conventional extracapsular surgical technique, including phacoemulsification, and the posterior capsule C remains intact. The fiber optic sleeve 3 is attached at the forefront of a phacoemulsification instrument 1. Optical fiber bundles 4 are shown extending from the sleeve 3. For the application disclosed, the fiber optic sleeve 3 is utilized for the purposes of endoillumination, video transmission, and application of photoablative laser energy to the pars plicata of the ciliary body for treatment of glaucoma.

FIG. 3 is an enlarged longitudinal schematic cross-sectional view of the present invention. The fiber optic sleeve has a proximal (leading) end 5 and a distal (trailing) end 6. With continuing reference to FIG. 3, the fiber optic assembly 3 consists of an elongated standard cannula adaptor 7 at the distal end 6 that is continuous with a frustoconical nipple 8, extending to cap 9, and then to a tapered applicator tip 10. An annular chamfer 11 and adjacent lipped flange 12 on the interior surface of the frustoconical nipple 8 permit insertion and securing of an internal coupler in the chamber 13 or for receiving an O-ring 14, which provides a liquid-tight seal when the sleeve is assembled on the surgical instrument. It is contemplated that other types of securing means such as locking rings can be used to secure the fiber optic sleeve member to the forefront of a surgical instrument. A circumferential lip 27 is provided at the distal end for facilitating installation of the sleeve 3 on a surgical instrument in preparation for use. The entire longitudinal length of the fiber optic sleeve 3 is approximately one inch.

The fiber optic sleeve 3 of the present invention is constructed of soft plastic material containing one or multiple fiber optic bundles. A fiber bundle 15 is shown in FIG. 3A and FIG. 3B. Material used in construction consists of vinyl plastic or other commercially available non-toxic medical grade plastic. Fiber optic bundles 15 contained within the body of the sleeve are constructed of commercially available quartz or zirconium fluoride optical fibers. The size of the central cylindrical bore 16 can be controlled during the manufacturing process, so that the fiber optic sleeve may be adaptable to a variety of surgical instruments. One or two portals 29 at the proximal end of the sleeve can be constructed at the time of manufacture to allow for flow of fluid between the fiber optic sleeve and the surgical instrument contained in its bore. Fluid entry allows maintenance of globe pressure and prevents excess heating of the laser element.

The cap 9, nipple 8 and cannula adaptor 7 are preferably encased by opaque silicone, tetrafluorethylene coating, or polyethylene cladding, which enhances optical transmission and also forms a protective sheath. The extent of cladding can be varied depending on the amount and direction of light transmission desired; cladding that terminates one millimeter from the proximal end of the applicator tip 10 would provide diffuse illumination, whereas cladding to the most anterior edge of the applicator tip 10 may be desirable in situations where a more focused beam is necessary. The face 18 of the proximal tip 10 is unclad and unencapsulated to provide uninterrupted application of light for illumination, microendoscopy, or laser beam application.

Coupling to standard sources for video, illumination or video is secured at the distal portion of the fiber optic sleeve 3 by standard methods. Optical fiber couplers are well known in the prior art, for example see U.S. Pat. No. 4,089,584 of Christopher E. Polczynski. In FIG. 3 a recessed, female receptor well 19 at the distal face of the cannula adaptor 7 serves to connect to an external male fiber optic cable (not shown). Details of alternative embodiments are shown in FIGS. 3A and 3B. The embodiment of FIG. 3A comprises an internally threaded annular female well 19A having an accurately machined surface of revolution to interfit with a corresponding threaded male connector fiber optic source (not shown). The flat base of the receptor well 19A allows for a secure fit and good light transmitting connection between the fiber optic bundle from the light source and the optical fibers 15 in the sleeve 3. The number and placement of individual optical fibers arranged in receptacles in the receptor well 19 can be controlled during the manufacturing process.

Alternatively, the receptacle well of FIG. 3B is shown as a threadless cone 19B having a gradual internal taper for receiving a similarly tapered, mating end of the fiber optic cable from the light source [to an annular diameter smaller than the connecting fiber optic source]. In this arrangement, an external fiber optic cable is precision formed to mate snugly within the receptacle well 19B. In addition, the posterior end 6 can be attached to a laser catheter assembly by means of a conventional coupler or heat shrink wrap.

Figure 4:
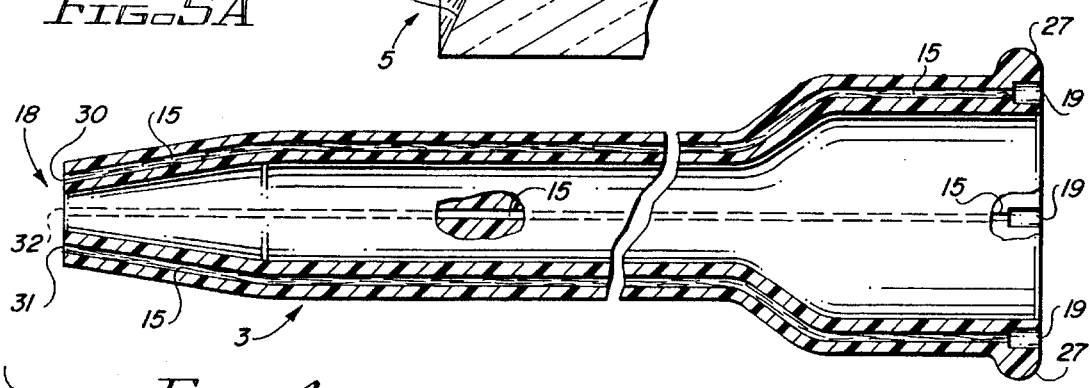
FIG. 4 is a schematic sectional view of an alternative embodiment of the invention.

FIG. 4 shows a tangential cross-sectional representation of the present invention. The fiber optic sleeve 3 consists of individual tracts of fiber optic bundles 15 of 500 to 600 micron quartz fibers having a bend radius of 4 centimeters or less that are incorporated within the body of the sleeve 3.

The fiber optic bundles 15 within the sleeve 3 can be arranged in distinct radially-spaced coherent light conducting portions, or in fiber bundles having spatial fiber distribution. In accordance with one particular feature of the invention, the tips of the optical fibers within the bore of the sleeve are recessed slightly for providing a collimated output beam. It is contemplated that a lens such as the lens 28 of FIG. 4A can be fused at the proximal end of the fiber optic bundle for focusing laser energy 30, or at the proximal end of the fiber optic bundle for illumination 31, or at the proximal end of the fiber optic bundle for endoscopy 32. Alternatively, an end piece 33 bearing a plurality of lenses 28 for the respective bundles 15 at their respective terminations 30, 31 and 32 can be installed at the end face 18 of the sleeve 3. Such a lens may be manufactured with a combination of convex, concave or flat surfaces. In the example of FIG. 4A, a plano-concave lens is shown.

Figure 5:
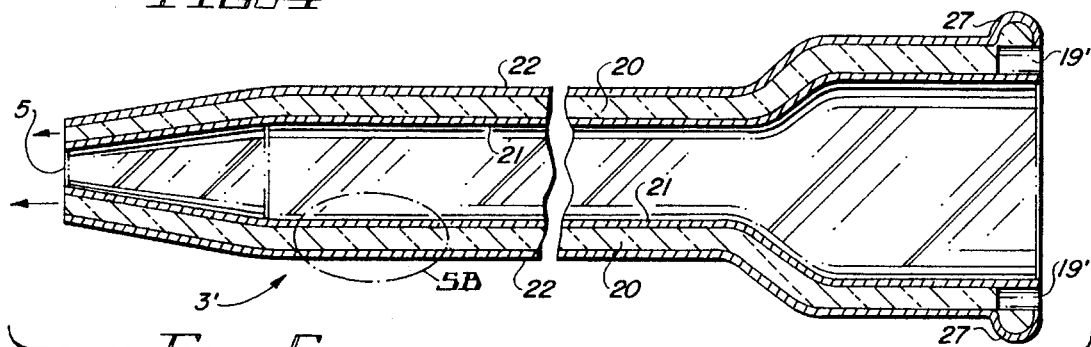
FIG. 5 is a schematic sectional view of still another embodiment of the invention.
Figure 5B:
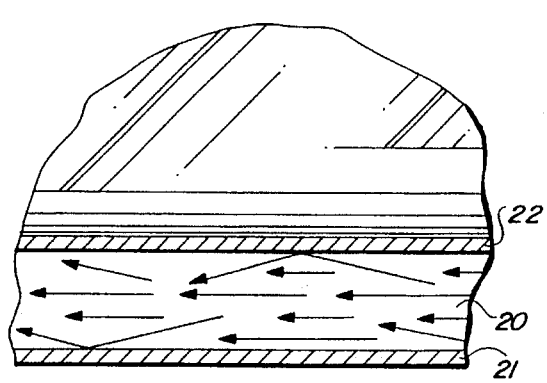
FIG. 5B is an enlarged schematic view in cross section of a wall portion of the embodiment of FIG. 5.

FIG. 5 shows an alternative embodiment of the present invention consisting of a sleeve 3' of optically clear flexible plastic 20 encased on its outer 21 and inner 22 surfaces by a thin layer of silicone cladding or opaque, non-toxic plastic capsule with a low index of refraction, or by a reflective coating, such as polytetrafluoroethylene, which enhances the optical transmission of the fiber optic sleeve. In this embodiment, the fiber optic bundles 15 are omitted because the entire sleeve 3' serves as an optical waveguide as indicated in FIG. 5B. The couplers 19', of which two are shown, are regularly spaced about the periphery and serve to couple the fiber optic bundles from a light source (not shown) into the optically clear plastic 20 for transmission of light to the tip end 5. Alternatively a diffusing collar may be provided, interposed between the light cable(s) and the sleeve 3'.

Preferably, the end face at the tip end 5 of the sleeve 3' should be beveled or angled inwardly so that the light emanating from the end face is directed at an angle radially inward toward the centerline of the embodiment. This is represented schematically in the enlarged schematic view of FIG. 5A which shows the end of the sleeve 3' encompassing a needle 4 and having a beveled end surface 30 extending at an angle α to a plane normal to the needle 4. The central axis of the needle 4 is represented by the broken line 32. The conical beam of light emanating from the beveled surface 30 is represented by the dashed lines 34, 35. The dashed line 34 intersects the axis line 32 at the same angle α. The inner surface 22 of the sleeve 3' is spaced from the needle 4 by a dimension s.

In practice, the angle α is a function of the dimensions of the needle 4 and the sleeve 3'. For a needle 4 having a diameter of 1 mm and projecting from the end 5 of the sleeve 3' by 2 mm, with sleeve wall thickness equal to 0.5 mm and spacing S also equal to 0.5 mm, the angle α should be approximately 23 degrees. If the spacing S is reduced to 0.25 mm, the angle α should be slightly less than 20 degrees. Angle α can actually be calculated by determining its tangent: i.e., the distance from the outer surface of the sleeve 3' to the centerline 32 divided by the distance from the end 5 to the intersection of the light cone line 34 with the centerline 32. In such an arrangement, the light cone illuminates the field of view for approximately 1.5 mm beyond the needle tip and approximately 0.75 mm of the end of the needle 4.

Figure 6:
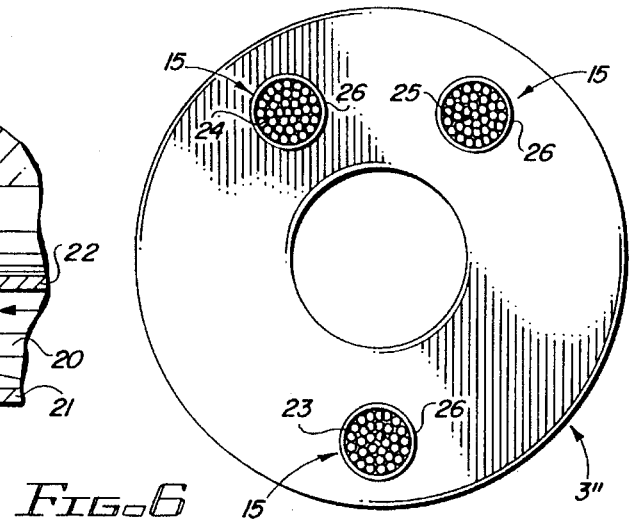
FIG. 6 is an enlarged schematic cross-sectional view showing details of the embodiment of FIG. 4.

FIG. 6 illustrates an alternative embodiment of the fiber optic sleeve 3" that incorporates multiple groups of fiber optic bundles 15 of optically segregated fibers for purposes of illumination 23, laser delivery 24, and microendoscopy 25 contained within the body of the sleeve. Each group of bundles 15 is positioned within a corresponding hollow tube 26 extending the length of the sleeve 3. Segregated optical fiber bundle groups are coupled at the distal end to conventional delivery systems for illumination, laser delivery and microendoscopy for video broadcast. It will be understood that the optical fibers in the bundle for microendoscopy must be maintained in the same orientation throughout their length in order that the pixel juxtaposition of the display will accurately represent the optical field of view. Optical segregation is accomplished by encapsulation of optic fiber bundles by optically opaque cladding on the inner surface of the hollow tube 26 identical to that used on the external and internal surfaces of the sleeve 3' in the embodiment of FIG. 5.

Operation in Use.

The operation of the system is as follows:

A light cable, laser cable or video cable (not shown) is connected at a receptacle well 19 situated in the terminal rim 27 of the fiber optic sleeve 3. A fiber optic bundle conducts light between the attachment at the receptacle well 19, through the wall of the fiber optic sleeve cannula 7, cap 8, cap 9 and proximal face of the fiber optic applicator tip 10. Fiber optic bundles 15 terminating at the proximal face of the fiber optic sleeve 3 provide light to illuminate the operative area of regard, or may provide laser energy for treatment of intraocular structures. Separate and coherent fiber optic bundles 25 similarly coursing within the walls of the fiber optic sleeve, provide intraocular endoscopy. Saline fluid to maintain globe pressure enters from the contained surgical instrument and travels within the hypodermic lumen to be discharged at the open applicator tip 16 or portals 29 of the fiber optic sleeve. Operation is the same for illumination using the sleeve 3' of FIG. 5 by coupling the light cable directly to the sleeve 3'.

Although there have been described hereinabove various specific arrangements of a fiber optic sleeve for surgical instruments in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A disposable light transmitting sleeve, for engagement with a surgical instrument, comprising:

a generally tubular structure with proximal and distal ends, the structure being in the form of an elongate hollow shell shaped for attachment to a surgical instrument and formed of soft, flexible, non-toxic medical grade plastic material extending between inner and outer walls, said tubular structure further including inner and outer cylindrical surfaces; and means for controlling and directing optical radiation internally between said walls and substantially along the sleeve between said ends comprising coatings on said surfaces selected to conduct and facilitate light transmission within the sleeve.

2. A sleeve as defined in claim 1 wherein said radiation controlling and directing means further comprise the plastic material between the inner and outer cylindrical surface coatings.

3. A sleeve as defined in claim 2 wherein said coatings comprise thin layers of silicone cladding.

4. A sleeve as defined in claim 2 wherein said coatings consists of polytetrafluorethylene to provide optical radiation reflectivity.

5. A sleeve as defined in claim 2 having a terminal surface at the proximal end of the tubular structure which is selectively shaped to direct transmitted optical radiation to the vicinity of the end of the associated surgical instrument.

6. A sleeve as defined in claim 5 wherein said terminal surface is beveled at a selected angle $\alpha$ relative to a plane normal to the central axis of the sleeve and associated surgical instrument.

7. A sleeve as defined in claim 2 further including means for coupling optical radiation to the plastic material between said inner and outer cylindrical surface coatings, said coupling means being situated at a proximal end surface of said tubular structure and adapted to engage cable means coupled to a light source.

8. A sleeve as defined in claim 1 wherein the material of said sleeve has an index of refraction which exceeds the index of refraction of the optical radiation controlling and directing means.

9. A disposable light transmitting sleeve, for engagement with a surgical instrument, comprising:

a generally tubular structure with proximal and distal ends, the structure being in the form of an elongate hollow shell shaped for attachment to surgical instrument and formed of soft, flexible, non-toxic medical grade plastic material extending between inner and outer walls; and means for controlling directing optical radiation internally between said walls and substantially along the sleeve between said ends;

wherein the optical radiation controlling and directing means comprise a plurality of optical fibers embedded within the plastic material and extending substantially throughout the length of the sleeve, said optical fibers being arranged in optically segregated fiber optic bundle groups for utilization in endolaser application in conjunction with endoillumination and intraocular microendoscopy, respectively;

each of said optically segregated fiber optical bundle groups being positioned within a corresponding hollow tube extending the length of the sleeve, the inner surface of each of said hollow tubes being coated with optically opaque cladding to provide total internal reflection of optical radiation within the tube.

10. A sleeve as defined in claim 9 further including means for coupling the fiber optic bundle groups respectively to conventional delivery sources for illumination, laser delivery or video imaging.

11. A sleeve as defined in claim 9 further including an adaptor member for coupling the optical fibers to an external source of optical radiation.

12. A sleeve as defined in claim 11 in which said adaptor member includes a cylindrical, threaded female receptor well precisely machined to interfit with an external male cable connector for receiving optical radiation from an external source.

13. A sleeve as defined in claim 11 wherein said adaptor member includes a gradually tapered unthreaded receptor well for frictional engagement with a connector for receiving optical radiation from an external source.

14. A sleeve as defined in claim 9 wherein each of the fiber optic bundle groups terminates in a fused lens at the proximal end thereof for focusing optical radiation transmitted along the bundle group.

15. A sleeve as defined in claim 9 further including an end piece bearing a plurality of lenses fused to the terminal ends of the fiber optic bundle groups for focusing optical radiation transmitted thereby.

16. A disposable fiber optic sleeve for use with a surgical instrument comprising:

a generally cylindrical body of soft medical-grade plastic material in the form of a shell extending about a hollow interior;

the interior of said body having means for engaging the terminal end of a surgical instrument on which it is to be mounted;

said body having a proximal end and a distal end, the distal end being larger in diameter than the proximal end and sized to fit the terminal end of a surgical instrument on which it is to be mounted;

a plurality of optical fibers extending within the shell between the distal and proximal ends for conducting optical radiation to illuminate a surgical field adjacent the proximal end; and means at the distal end for coupling the optical fibers to an external source of optical radiation;

said optical fibers being organized in discrete optically segregated fiber optic bundles for conducting optical radiation from disparate radiation sources to a surgical field adjacent the proximal end;

each of said discrete bundles being installed within a hollow passage within said shell, the inner surface of said passage being coated with an optically opaque cladding to provide total internal reflection of optical radiation within the passage.

17. A sleeve as defined in claim 16 wherein the optical fibers are arranged in optically segregated fiber optic bundle groups for utilization in endolaser application in conjunction with endoillumination and intraocular microendoscopy, respectively.

* * * * *